United States Patent [19]

Chan

[11] Patent Number: 4,902,692
[45] Date of Patent: Feb. 20, 1990

[54] METHOD AND COMPOSITION FOR OPHTHALMIC ANESTHESIA USING RODOCAINE

[75] Inventor: Peter W. K. Chan, Culver City, Calif.

[73] Assignee: Iolab Corporation, Claremont, Calif.

[21] Appl. No.: 169,665

[22] Filed: Mar. 18, 1988

[51] Int. Cl.$^4$ .............................................. A61K 31/44
[52] U.S. Cl. .................................................. 514/299
[58] Field of Search ........................................ 514/299

[56] References Cited

U.S. PATENT DOCUMENTS 4,091,090  5/1978  Sipos ..................................... 514/330

OTHER PUBLICATIONS

Drug information page 1084, 1984.

*Primary Examiner*—Douglas W. Robinson
*Assistant Examiner*—Zohreh A. Fay
*Attorney, Agent, or Firm*—Benjamin F. Lambert

[57] ABSTRACT

Rodocaine or a pharmaceutically-acceptable salt thereof has been found to be an effective anesthetic in ophthalmology. Topical and injectable formulations are disclosed.

12 Claims, No Drawings

METHOD AND COMPOSITION FOR OPHTHALMIC ANESTHESIA USING RODOCAINE

BACKGROUND OF THE INVENTION

Local topical anesthetics for the eye are generally used with caution since the decrease in blinking and subsequent dehydration may cause damage to the corneal epithelium. For non-surgical situations, the eye care professional would want anesthesia in the eye which would last only as long as the desired procedure. Such a procedure may be quite short, and there is thus a need for a fast acting and yet transient topical anesthetic for the eye. Such an anesthetic would minimize the keratitis caused by the lack of or decreased rate of blinking.

Injectable anesthetics are used in the eye by retro-bulbar injection to prevent the eye muscles of the patient from moving during sugery. For example, during cataract surgery, the lens of the eye is replaced, and the ophthalmologist will normally anesthetize the retro-bulbar muscles and nerves to keep the eye still during the delicate procedure. Many such surgeons use a combination of drugs to achieve the proper anesthetic profile. For example, lidocaine may have a quick inset while bupivacaine provides a longer action. However, such mixing is an obvious disadvantage.

SUMMARY OF THE INVENTION

An ophthalmic anesthetic, particularly for topical use, has been found in rodocaine. Also part of the invention are ophthalmic pharmaceuticals which contain rodocaine.

DETAILED DESCRIPTION OF THE INVENTION

Rodocaine is the generic name for N-(2-chloro-6-methylphenyl)octahydro-trans-1H-pyrindine-1-propanamide. Another, chemical name for this compound is trans-6'-chloro-2,3,4,4a,5,6,7,7a-octahydro-1H-1-pyrindine-1-propiono-o-toluidide. This compound has the following formula (I):

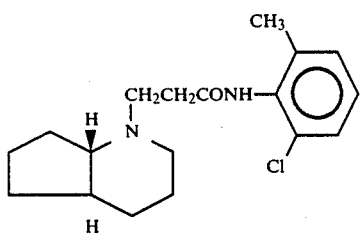

The synthesis of rodocaine is described in U.S. Pat. No. 3,679,686 to Hermans et al. in Example V.

The pharmaceutically-acceptable, acid-addition salts of rodocaine may be prepared by reaction of the rodocaine free base with the desired acid in the general manner known in the art. Representative salts of the compounds of formula (I) which may be used include those made with acids such as hydrochloric, hydrobromic, hydroiodic, perchloric, sulfuric, nitric, a phosphoric, acetic, propionic, glycolic, lactic, pyruvic, malonic, succinic, maleic, fumaric, malic, tartaric, citric, benzoic, cinnamic, mandelic, methane-sulfonic, ethane-sulfonic, hydroxyethanesulfonic, benzene-sulfonic, p-toluene sulfonic, cyclohexanesulfamic, salicylic, p-aminosalicylic, 2-phenoxybenzoic, 2-acetoxybenzoic or a salt made with saccharin.

The use of rodocaine or its salt according to the present invention may be topically or by injection. A typical injection embodiment of the invention would be by retro-bulbar injection to anesthetize the muscles of the patients eye so that the eye will stay still and be free of pain during surgery, e.g. during cataract surgery. The injection vehicles may be any of the typical injection vehicles used in the ophthalmic art, e.g. saline with preservative. The formulation of such an injection may be carried out in a manner similar to Xylocaine ®, Lidocaine which is a 4% sterile solution containing hydrochloric acid or sodium hydroxide to adjust the pH to 5.0 to 7.0. The concentration of rodocaine or its salt in such a sterile solution would be about 2% or less, e.g. 0.25% w/v. As used herein, "w/v" indicates weight in grams per milliliter of volume. Thus, 2.5 mg per milliliter would be about 0.25% w/v.

In the injectable embodiment of the invention, the rodocaine or its salt may be combined with a vasoconstrictor such as epinephrine to prevent transport of the anesthetic away from the site of injection. Thus, the anesthetic would stay longer in the site of injection and achieve its desired effect. The amount of epinephrine which could be used in such a combination would be on the order of about 0.001% to 0.002% w/v.

For topical applications, the vehicle used to transport the rodocaine or its salt can be an aqueous saline solution with or without a significant amount of polymer to aid retention in the eye. Polymers which can be used include ethyl cellulose, hydroxypropylmethyl cellulose, carboxymethyl cellulose or polyvinylalcohol in an amount of about 0.5 to 1% w/v. One may formulate the rodocaine or its salt in a manner similar to various commercial artificial tear preparations or may even add the rodocaine or its salt to such preparations to provide an effective topical anesthetic. Commercial artificial tear preparations which can be used include Tearisol from Iolab Pharmaceuticals of Claremont, California, Liquifilm Tears from Allergan Pharmaceuticals, Inc. of Irvine, California and similar preparations. Preservatives may be used, particularly if a multi-use container is contemplated. The preservative of the commercial formulation may be required to be changed in view of possible interaction, e.g. precipitation, with the rodocaine or its salt. Thus, benzalkonium chloride may be deleted with substitution in its place of thimerosal, e.g. 0.002% w/v, chlorobutanol, e.g. 0.5% w/v or methylparaben and/or propylparaben.

The rodocaine or its salt may be used in the topical formulation in an amount of about 1% or less by weight of the vehicle, e.g. 0.5 to 1% by weight based on the volume of said vehicle. Lower concentrations of 0.5, 0.25 or even 0.1% or less of the rodocaine or its salt may be used.

Compared with proparacaine and benoxinate, where corneal sensitivity is blocked for 15–20 minutes with a baseline recovery in 65–80 minutes, rodocaine produces a maximal block within 5 minutes and by 10 minutes, corneal sensitivity increased until it is back to normal at 35–60 minutes.

The corneal epithelial toxicity of rodocaine in concentration of 0.4%, 0.22% and 0.0875% w/v in both preserved and unpreserved formulations indicates minimal effects on corneal epithelium when compared to untreated and phosphate buffered saline treated controls.

EXAMPLE 1

Rodocaine is formulated into seven concentrations by solubilizing in phosphate buffered saline. After baseline corneal sensitivity is established in New Zealand white rabbits using a Cochet-Bonet anesthesiometer, one 25 $\mu$l drop of rodocaine is instilled in four eyes per dose. Corneal sensitivity is then measured every five minutes until the baseline is regained.

REFERENCE EXAMPLE 1

In a manner similar to the above, proparacaine, in a concentration of about 0.5% w/v and benoxinate in a concentration of about 0.4% w/v is formulated in commercially available preparations.

What is claimed is:

1. A method for topically anesthetizing the eye which comprises administering a pharmaceutically effective amount of anesthetic selected from the group consisting of rodocaine or a pharmaceutically-acceptable, acid-addition salt thereof to the eye.

2. The method of claim 1, wherein said anesthetic is contained in an ophthalmic liquid vehicle.

3. The method of claim 2, wherein said anesthetic comprises about 1% or less by weight based on the volume of said vehicle.

4. The method of claim 3, wherein said anesthetic comprises about 0.5 to 1% by weight based on the volume of said vehicle.

5. The method of claim 3, wherein said anesthetic comprises about 0.5% or less by weight based on the volume of said vehicle.

6. The method of claim 3, wherein said anesthetic comprises about 0.25% or less by weight based on the volume of said vehicle.

7. The method of claim 3, wherein said anesthetic comprises about 0.1% or less by weight based on the volume of said vehicle.

8. The method of claim 1, wherein said anesthetic is rodocaine.

9. The method of claim 1, wherein said anesthetic is a pharmaceutically-acceptable salt of rodocaine.

10. A method for inducing retro-bulbar anesthesia which comprises injecting into the retro-bulbar muscles, a liquid pharmaceutical composition comprising a pharmaceutically effective amount of an anesthetic selected from the group consisting of rodocaine or a pharmaceutically-acceptable, acid-addition salt thereof.

11. A method for inducing anesthesia in the eye which comprises injecting an anesthetic selected from the group consisting of rodocaine or a pharmaceutically acceptable, acid addition salt thereof in an amount sufficient to induce anesthesia and in conjunction with an effective amount of a vasocontrictor.

12. A method of claim 11, wherein said vasoconstrictor is epinephrine.

* * * * *